United States Patent [19]

WoldeMussie et al.

[11] Patent Number: 6,077,839
[45] Date of Patent: Jun. 20, 2000

[54] METHOD FOR REDUCING INTRAOCULAR PRESSURE IN THE MAMMALIAN EYE BY ADMINISTRATION OF GAMMA AMINOBUTYRIC ACID (GABA) AGONISTS

[75] Inventors: Elizabeth WoldeMussie, Laguna Niguel; Guadalupe Ruiz, Corona, both of Calif.

[73] Assignee: Allergan Sales, Inc., Irvine, Calif.

[21] Appl. No.: 07/856,012

[22] Filed: Mar. 19, 1992

[51] Int. Cl.⁷ ........................ A61K 31/55; A61K 31/445; A61K 31/385; A61K 31/205
[52] U.S. Cl. ........................ 514/220; 514/315; 514/439; 514/554; 514/913
[58] Field of Search ................................ 514/220, 554, 514/315, 439, 913

[56] References Cited

U.S. PATENT DOCUMENTS

| | | | |
|---|---|---|---|
| 3,467,756 | 9/1969 | Stone | 424/283 |
| 3,644,643 | 2/1972 | Krantz, Jr. | 424/319 |
| 4,171,377 | 10/1979 | Green et al. | 424/319 |
| 4,197,301 | 4/1980 | Smith et al. | 424/251 |
| 4,322,440 | 3/1982 | Fish et al. | 424/319 |
| 4,363,818 | 12/1982 | Gottlieb | 424/319 |
| 4,565,821 | 1/1986 | Chiou | 514/327 |
| 4,837,021 | 6/1989 | Andermann et al. | 424/602 |
| 5,066,664 | 11/1991 | Glouchowski | 514/377 |
| 5,091,528 | 2/1992 | Glouchowski | 544/105 |

OTHER PUBLICATIONS

J.A. Pino Capote, *Decarease in Intraocular Pressure by I.V. or Conjunctival Diazepam*, British Journal of Anaesthesia, vol. 50, No. 8 1978, p. 865.

L. Berrino et al., *Participation of Alpha2–Adrenergic, Opiate, Peptidergic Gabaergic, and Protaglandin Mechanism on Intraocular and Cardiovascular Effects of Clonidine in Conscious Rabbits*, Current Therapeutic Research, vol. 42, No. 5, 1987, pp. 790–806.

D. De Santis et al., *Central Regulation of Intraocular Pressure and Cardiovascular Apparatus with Clonidine in Conscious Rabbits*, ACTA Pharmacologica Sinica, vol. 9, No. 4, 1988, pp. 323–326.

Mohamed H. Al–Abrak, *Diazepam and Intraocular Pressure*, British journal o f anaesthesia, vol. 50, No. 7, Jul. 1978, p. 866.

R. J. Fragen, et al., *The Effect of Midazolam Maleate and Diazepam on Intraocular Pressure in Adults*, Arzneim Forsch/Drug Res., 31(II), No. 12a (1981), pp. 2273–2275.

Stanley W. Hymans, et al., *Glaucoma Due to Diazepam*, Clinical and Research Reports, Am J Psychiatry, 134:4, Apr. 1977, pp. 447–448.

Winston Roberts, M.D., *The Use of Psychotropic Drugs in Glaucoma*, Dis. Nerv. Syst. (Suppl.) 29:, 1968, pp. 40–43.

Shader, R.I. & Di Mascio, A., *Psychotropic Drug Side Effects*, Baltimore, Williams and Wilkins, 1970, pp. 116–123.

Dermot F. Murphy, *Anesthesia and Intraocular Pressure* Anesth Analg, 1985, 64: 520–30.

C. T. Trew, et al., *Forum Intra–ocular pressure and premedication with oral diazepam*, Anaesthesia, 1982, vol. 37, pp. 339–340.

Embase Abstract of Klin. MBL . Augenheilk (Germany West), 1974, 165/6 (946–947), Kastner.

*Primary Examiner*—Marianne M. Cintins
*Attorney, Agent, or Firm*—Gabor L. Szekeres; Robert J. Baran; Martin A. Voet

[57] ABSTRACT

Ophthalmic compositions and a method are disclosed for treating glaucoma and/or ocular hypertension in the mammalian eye by topically administering to the mammalian eye the ophthalmic composition of the invention which contains as the active ingredient one or more gamma aminobutyric acid agonist compounds. Examples of gamma aminobutyric acid agonists utilized in the ophthalmic composition and method of treatment are: gamma aminobutyric acid (GABA), 5-(aminomethyl)-3(2H)-isoxazolone (muscimol), 4,5,6,7-tetrahydroisoxazolo[5,4-c]pyridin-3-ol (THIP) and a pharmaceutically acceptable salt of 4,5,6,7-tetrahydroisoxazolo[5,4-c]pyridin-3-ol, piperidine-4-sulfonic acid and a pharmaceutically acceptable salt of piperidine-4-sulfonic acid, 3-(2H)-isothiazolone, 5-(aminomethyl) (thiomuscimol), 7-chloro-1,3-dihydro-1-methyl-5-phenyl-2H-1,4-benzodiazepin-2-one (diazepam), 7-chloro-1-[2-(diethylamino)ethyl]-5-(2-fluorophenyl)-1,3-dihydro-2H-1,4-benzodiazaepin-2-one (flurazepam) and a pharmaceutically acceptable salt of 7-chloro-1-[2-(diethylamino)ethyl]-5-(2-fluorophenyl)-1,3-dihydro and 7-chloro-N-methyl-5-phenyl-3H-1,4-benzodiazepin-2-amine 4-oxide (chlordiazepoxide) and a pharmaceutically acceptable salt of 7-chloro-N-methyl-5-phenyl-3H-1,4-benzodiazepin-2-amine 4-oxide.

7 Claims, 2 Drawing Sheets

METHOD FOR REDUCING INTRAOCULAR PRESSURE IN THE MAMMALIAN EYE BY ADMINISTRATION OF GAMMA AMINOBUTYRIC ACID (GABA) AGONISTS

BACKGROUND OF THE INVENTION

1. Field of the Invention

The present invention is directed to pharmaceutical compositions, and primarily to topically applied ophthalmic compositions comprising as the active ingredient one or more gamma amino butyric acid agonist compounds. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye.

2. Brief Description of the Prior Art

Glaucoma is an optical neuropathy associated with elevated intraocular pressures which are too high for normal function of the eye, and results in irreversible loss of visual function. It is estimated in medical science that glaucoma afflicts approximately 2 per cent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma.

Gamma amino butyric acid ($H_2N(CH_2)_3COOH$, GABA) is a natural metabolite, a break-down product of glutamine and a major inhibitory neurotransmitter. Its chemical structure can be described as an aliphatic carboxylic acid which carries an amino function on the terminal carbon of the aliphatic chain.

The concept of gamma amino butyric acid (GABA) receptors has been known in the biological sciences for a long time. According to the classical definition, GABA receptors of living organisms, (including mammals and particularly humans) are those biological receptor sites which are activated by GABA. Agonist of a receptor are those compounds or substances which bind to the receptor site and elicit a response. Accordingly, agonist of GABA receptors are those compounds which bind to and elicit a response on GABA receptor sites. The compound gamma aminobutyric acid itself by definition, is a GABA agonist, and several other GABA agonist are known in the pharmaceutical and related sciences.

The following patents (and other references) are believed to be pertinent as background to the present invention, either because they describe or relate to compounds or compositions for reducing intraocular pressure (anti-glaucoma), or because they relate to the biological activity of GABA or structurally related compounds.

U.S. Pat. No. 3,644,643 describes a process of systemically administering glycine (an amino acid) for the purpose of reducing intraocular pressure.

U.S. Pat. No. 4,837,021 describes an irrigating solution for irrigating exposed eye tissue during surgery for the purpose of preventing or ameliorating injury to the exposed eye tissue, which solution includes GABA or a functional equivalent analog.

U.S. Pat. No. 4,171,377 discloses an ophthalmic solution which is applied topically to injured or swollen cornea to reduce swelling and promote epithelial healing, which solution contains trans-4-(aminomethyl) cyclohexanecarboxylic acid (tranexamic acid) as the active ingredient.

U.S. Pat. No. 4,363,818 discloses a method for drying and diminution of cutaneous and mucosal lesions by topically applying a solution which contains as the active ingredient ε-aminocaproic acid ($NH_2$-$(CH_2)_5COOH$) or other isomers of aminocaproic acid.

U.S. Pat. No. 4,322,440 refers to still earlier literature references regarding systemic administration of GABA agonists, and that such administration does not provide a useful anti-convulsant effect. The patent nevertheless describes amino carboxylic acids (and simple derivatives) where the carboxylic function and the amino function are separated by 3 or 4 methylene ($CH_2$) units, and which have anti-convulsant and anxiolytic activities.

Additional examples of background art to the present invention directed to intraocular hypotensive and anti-glaucoma agents can be found in the following U.S. Pat. Nos. 3,467,756; 4,197,301; 4,565,821; 5,066,664 and 5,091,528.

The foregoing and other anti-glaucoma and ocular hypotensive compounds and agents of the prior art do not provide such treatment or cure for glaucoma and ocular hypertension which is satisfactory in all respects. Therefore, the pharmacological and related arts continue searching for additional and better anti-glaucoma and ocular hypotensive agents. The present invention represents a significant advance step in this direction.

SUMMARY OF THE INVENTION

Surprisingly it has been discovered in accordance with the present invention that GABA agonists are effective as anti-glaucoma agents and as agents for reducing intraocular pressure, when such agonist agents are applied to the mammalian eye in a pharmaceutical composition, preferably in a topical ophthalmic composition. Accordingly, the present invention relates to a method of treating glaucoma, or ocular hypertension by administering to the mammalian eye an ophthalmic composition which contains an effective amount of a GABA agonist. Preferred examples of GABA agonists suitable as the active ingredients of the ophthalmic compositions of the invention are:

gamma aminobutyric acid (GABA);

5-(aminomethyl)-3(2H)-isoxazolone (muscimol);

4,5,6,7-tetrahydroisoxazolo[5,4-c]pyridin-3-ol hydrochloride (THIP-HCl) or other pharmaceutically acceptable salt of THIP;

piperidine-4-sulfonic acid or a pharmaceutically acceptable salt;

3-(2H)-isothiazolone, 5-(aminomethyl) (thiomuscimol);

7-chloro-1,3-dihydro-1-methyl-5-phenyl-2H-1,4-benzodiazepin-2-one (diazepam);

7-chloro-1-[2-(diethylamino)ethyl]-5-(2-fluorophenyl)-1,3-dihydro-2H-1,4-benzodiazaepin-2-one hydrochloride (flurazepam hydrochloride) or other pharmaceutically acceptable salt of flurazepam, and 7-chloro-N-methyl-5-phenyl-3H-1,4-benzodiazepin-2-amine 4-oxide hydrochloride (chlordiazepoxide HCl), or other pharmaceutically acceptable salt of chlordiazepoxide.

The ophthalmic compositions of the invention contain the active ingredient in a concentration range of approximately 0.1 to 5.0 per cent, weight by volume. The composition itself includes, in addition to the active ingredient, such excipients which are per se well known in the art for preparing ophthalmic compositions, particularly ophthalmic solutions. In accordance with the method of the invention the ophthalmic compositions, preferably ophthalmic solutions, are applied topically to the mammalian eye approximately 1 or 2 times daily.

DETAILED DESCRIPTION OF THE INVENTION

Figure 1:
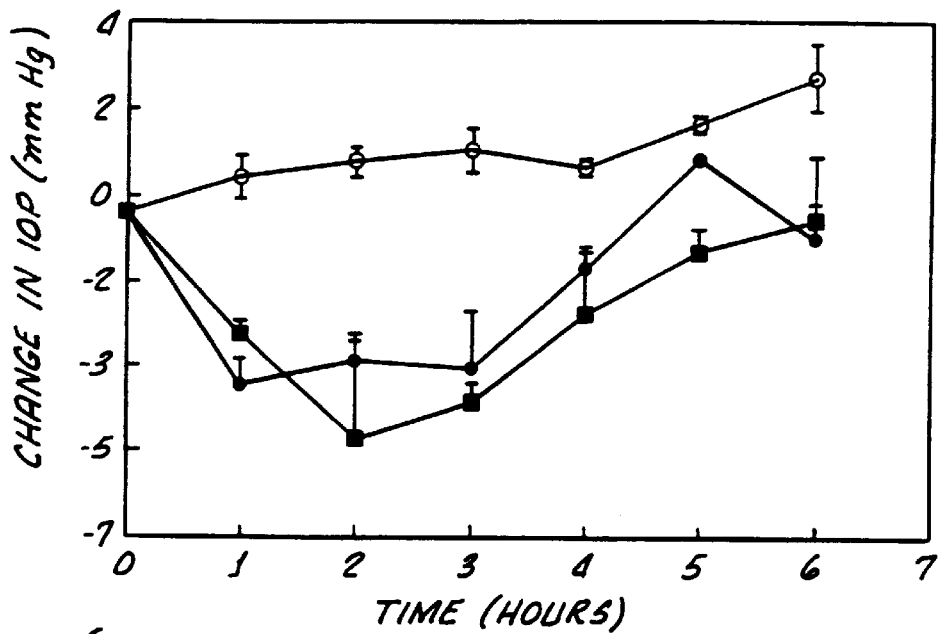
FIG. 1 is a graph showing the effect of topical administration of the drug muscimol on the intraocular pressure (IOP) in the rabbit eye.

The compounds which are utilized in accordance with the method of the present invention, and in the ophthalmic compositions of the present invention, are GABA agonists. In this regard the term "GABA agonist" is defined as in the pharmacological and related sciences where this term has a well accepted meaning. Briefly, GABA agonists are those compounds or substances which bind to GABA receptor sites and elicit a response. Specific and preferred examples of GABA agonist compounds which are utilized in accordance with the present invention are provided below.

Pharmaceutically acceptable salts of the GABA agonist compounds can also be used in accordance with the present invention, where the nature of the agonist compound permits the preparation of such salt. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

For reducing intraocular pressure in a mammalian eye (as for treatment of glaucoma in humans suffering from that condition) the active compounds (or mixtures or salts thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.1% to approximately 5% (weight by volume) and more preferably approximately 1% to approximately 3% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotension. An exemplary topical ophthalmic formulation is shown below in Table I. The abbreviation q.s. means a quantity sufficient to effect the result or to make volume.

TABLE I

| Ingredient | Amount (% W/V) |
| --- | --- |
| Active Compound in accordance with the invention, | about 0.1 to about 5 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |

Purified Water as needed to make 100%

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The ophthalmic solution (ocular drops) may be administered to the mammalian eye as often as necessary to maintain an acceptable level of intraocular pressure in the eye. In other words, the ophthalmic solution (or other formulation) which contains the GABA agonists as the active ingredient, is administered to the mammalian eye as often as necessary to maintain the beneficial hypotensive effect of the active ingredient in the eye. Those skilled in the art will recognize that the frequency of administration depends of the precise nature of the active ingredient and its concentration in the ophthalmic formulation. Within these guidelines it is contemplated that the ophthalmic formulation of the present invention will be administered to the mammalian eye approximately once or twice daily.

Examples of GABA agonists which are used as the active effective ingredients in the ophthalmic compositions of the present invention are described and shown below:

Gamma aminobutyric acid is a naturally occurring neurotransmitter which is believed to be a metabolic product of glutamic acid. This compound is also known by the abbreviated name GABA. GABA is commercially available in the United States, from several sources, for example from Aldrich Chemical Company of Milwaukee, Wis. (Aldrich), and Research Biochemicals Inc. of Natick, Mass. (Research Biochemicals). Ophthalmic preparations which contain GABA as the active hypotensive ingredient in accordance with the present invention, contain this drug in the approximate concentration range of 0.1 to 5 per cent, weight by volume. GABA is a preferred ocular hypotensive agent/active ingredient amongst the several GABA agonists in the methods of treatment and pharmaceutical, particularly ophthalmic, compositions of the present invention.

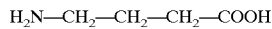

GABA

Another GABA agonist which is highly preferred amongst the several GABA agonist as the ocular hypotensive agent of the method and compositions of the present invention is 5-(aminomethyl)-3(2H)-isoxazolone. This compound is also known as muscimol, and can be isolated from mushrooms of the *Amanita muscaria* species. The compound can also be synthesized, for example by the processes described by Gagneaux et al. in *Tetrahedron Letters* 1965 p.813, and by Goth et al. in *Helv. Chim. Acta,* 50, 137 (1967). The drug is also available commercially from Research Biochemicals. The concentration of muscimol in the ophthalmic compositions formulated in accordance with the present invention is in the 0.1 to 5 per cent (weight by volume) range.

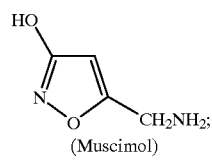

(Muscimol)

Still another exemplary GABA agonist which can be used as the active ingredient in the method of treatment and ophthalmic composition of the present invention is 4,5,6,7-tetrahydroisoxazolo[5,4-c]pyridin-3-ol hydrochloride (THIP HCl) or other pharmaceutically acceptable salt of THIP. This compound can be synthesized in accordance with the teachings of U.S. Pat. No. 4,278,676, the specification of which is expressly incorporated herein by reference. This example of the GABA agonists used in the present invention, as well as all other specifically named examples are commercially available from Research Biochemicals. The concentration of THIP-HCl (or of other pharmaceutically acceptable salt of THIP) in the ophthalmic compositions formulated in accordance with the present invention is in the 0.1 to 5 per cent (weight by volume) range.

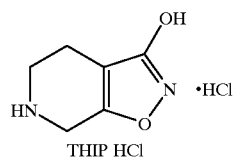

THIP HCl

Yet another example of a GABA agonist which can be used in the methods of treatment and ophthalmic compositions of the present invention is piperidine-4-sulfonic acid, or a pharmaceutically acceptable salt of piperidine-4-sulfonic acid. This compound is available from several commercial sources in the United States. The drug is present in the range of approximately 0.1 to 5 per cent (weight by volume) in the ophthalmic compositions of the present invention.

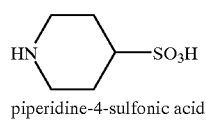

piperidine-4-sulfonic acid

3(2H)-Isothiazolone, 5-(aminomethyl), also known as thiomuscimol, is a further GABA agonist which is utilized as the ocular hypotensive agent in the method and formulation of the present invention. The drug is available from Research Biochemicals, and can be synthesized in accordance with the procedure set out by Lykkeberg et al. *Acta Chem. Scand.,* Ser. B, B30(8) 781–5 (1976). The approximate concentration of this drug in the formulations of the present invention is in the range of 0.1 to 5 per cent, weight by volume.

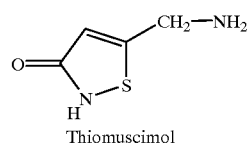

Thiomuscimol 7-chloro-1,3-dihydro-1-methyl-5-phenyl-2H-1,4-benzodiazepin-2-one (diazepam), 7-chloro-1-[2-

(diethylamino)ethyl]-5-(2-fluorophenyl)-1,3-dihydro-2H-1,4-benzodiazaepin-2-one hydrochloride (flurazepam hydrochloride), or other pharmaceutically acceptable salts of flurazepam, and 7-chloro-N-methyl-5-phenyl-3H-1,4-benzodiazepin-2-amine 4-oxide hydrochloride (chlordiazepoxide HCl) or other pharmaceutically acceptable salt of chlordiazepoxide, serve as examples of GABA agonists of the benzodiazepine structure, which can be utilized as the ocular hypotensive agents in the ophthalmic compositions of the present invention. The approximate concentration of these agents in the ophthalmic compositions is also in the 0.1 to 5 per cent (weight by volume) range. These benzodiazepine drugs can be obtained commercially. Diazepam can be prepared in accordance with the teachings of U.S. Pat. No. 3,371,085, chlordiazepoxide can be prepared in accordance with U.S. Pat. No. 2,893,992 and flurazepam can be prepared in accordance with U.S. Pat. No. 3,299,053. The specification of these three United States patents are incorporated herein by reference.

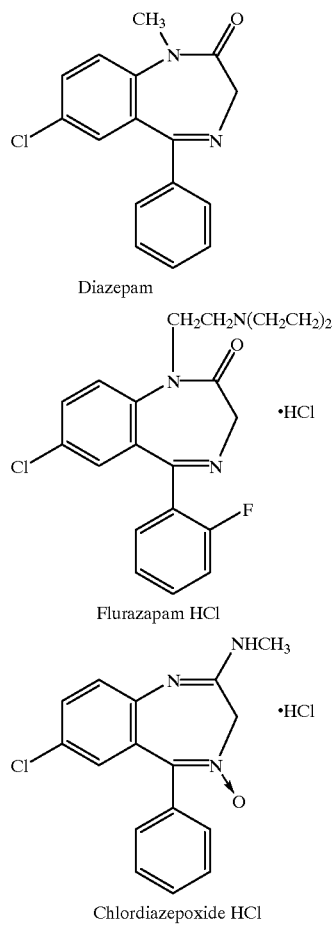

Diazepam

Flurazapam HCl

Chlordiazepoxide HCl

The anti-glaucoma/ocular hypotensive effect, namely the effect of the GABA agonists to reduce intraocular pressure, was confirmed by assay procedures conducted on New Zealand-cross Dutch belted (NZ×DB) rabbits, and in owl monkeys.

In the assay procedures the test compounds were topically applied into one eye in normal saline solution (10 μl in owl monkeys and 25 μl in rabbits). The other eye was left untreated.

Intraocular pressure (IOP) was measured in the assays with pneumotonometer (BIO-RAD/Digilab), and pupil diameter (PD) was measured with a ruler (OPtistick®, Allergan), every one or two hours from time zero (time of administration) to 6 hours. results are mean ±S.E. of three or more animals. Control animals were treated in the eye with the normal saline solution vehicle only. The graphs of FIGS. 1, 2, and 3 each show the results obtained in the control animals with the normal saline solution as well.

Thus, FIG. 1 demonstrates the efficacy of muscimol in lowering the intraocular pressure (IOP) in the rabbit eye, for up to 6 hours after topical administration of 25 μl of, respectively, 1.0 and 2.0 per cent (weight by volume) of this drug to the eye.

Figure 2:
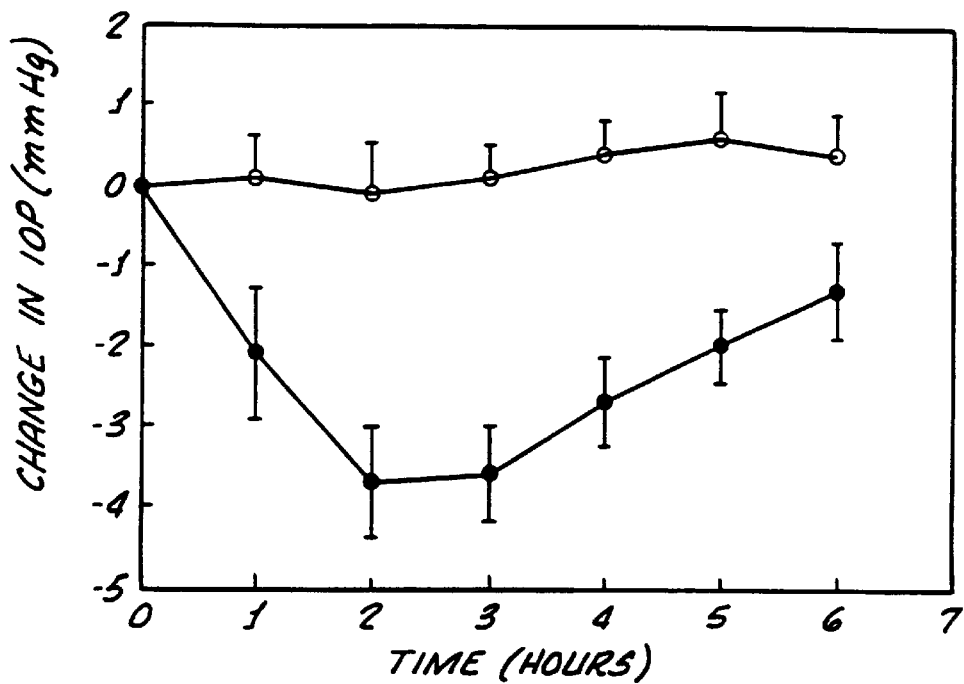
FIG. 2 is a graph showing the effect of topical administration of the drug gamma aminobutyric acid (GABA) on the intraocular pressure (IOP) in the rabbit eye.

FIG. 2 demonstrates the hypotensive effect of GABA in the eyes of rabbits for up to six hours after administration of 25 μl of a 2 per cent (weight by volume) of this drug in the eye.

Figure 3:
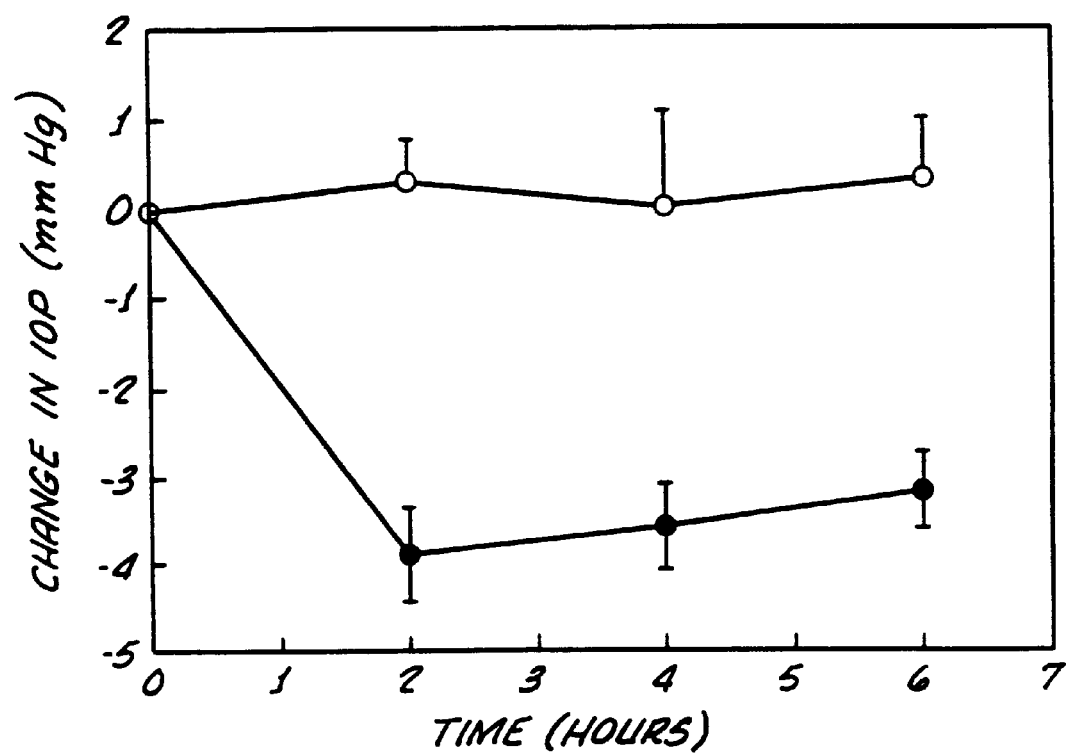
FIG. 3 is a graph showing the effect of topically applied muscimol on the intraocular pressure (IOP) in the eyes of owl monkeys; this graph as well as the graphs of FIGS. 1 and 2 also show the intraocular pressure (IOP) measured in control animals after topical application of the saline vehicle of administration.

FIG. 3 shows the hypotensive effect of the drug muscimol for up to 6 hours in the eyes of owl monkeys, after administration of 10 μl of 1 per cent (weight by volume) of the drug in the eye.

Several modifications of the present invention may become readily apparent to those skilled in the art in light of the present disclosure. Therefore, the scope of the present invention should be interpreted solely on the basis of the following claims, as such claims are read in light of the disclosure.

What is claimed is:

1. A method of treating animals of the mammalian species for the purpose of reducing intraocular pressure in the eye of the mammal, the method of treatment comprising the steps of administering to the mammal an ophthalmic solution which comprises as its active ingredient one or more gamma aminobutyric acid agonist compounds and wherein the active ingredient is present in the range of approximately 0.1 to 5 per cent weight by volume.

2. The method of treatment of claim 1 where the ophthalmic solution is adapted for administration to the eye of a mammal in the form of eye droplets.

3. A method of treating animals of the mammalian species for the purpose of reducing intraocular pressure in the eye of the mammal, the method of treatment comprising the steps of administering to the mammal an ophthalmic composition in the form of eye droplets which comprises as its active ingredient one or more gamma aminobutyric acid agonist compounds selected from a group consisting of:

gamma aminobutyric acid (GABA),
5-(aminomethyl)-3(2H)-isoxazolone (muscimol),
4,5,6,7-tetrahydroisoxazolo[5,4-c]pyridin-3-ol (THIP) and a pharmaceutically acceptable salt of 4,5,6,7-tetrahydroisoxazolo[5,4-c]pyridin-3-ol,
piperidine-4-sulfonic acid and a pharmaceutically acceptable salt of piperidine-4-sulfonic acid,
3-(2H)-isothiazolone, 5-(aminomethyl) (thiomuscimol),
7-chloro-1-[2-(diethylamino)ethyl]-5-(2-fluorophenyl)-1,3-dihydro-2H-1,4-benzodiazaepin-2-one (flurazepam) and a pharmaceutically acceptable salt of 7-chloro-1-[2-(diethylamino)ethyl]-5-(2-fluorophenyl)-1,3-dihydro-2H-1,4-benzodiazaepin-2-one, and
7-chloro-N-methyl-5-phenyl-3H-1,4-benzodiazepin-2-amine 4-oxide (chlordiazepoxide) and a pharmaceutically acceptable salt of 7-chloro-N-methyl-5-phenyl-3H-1,4-benzodiazepin-2-amine 4-oxide the concentration of the gamma aminobutyric acid agonist in the eye droplets being in the range of approximately 0.1 to 5 per cent, weight by volume.

4. The method of treatment of claim 2 wherein the eye droplets are administered to the patients 1 or 2 times per day.

5. The method of treatment of claim 3 wherein the eye droplets are administered to the patients 1 or 2 times per day.

6. The method of treatment of claim 5 where the gamma aminobutyric acid agonist is selected from a group consisting of gamma aminobutyric acid (GABA), and 5-(aminomethyl)-3(2H)-isoxazolone (muscimol).

7. The method of treatment of claim 6 wherein the gamma aminobutyric acid agonist is 5-(aminomethyl)-3(2H)-isoxazolone (muscimol).

* * * * *